United States Patent [19]

Tanabe et al.

[11] Patent Number: 4,960,883
[45] Date of Patent: Oct. 2, 1990

[54] PIPERAZINES AND HOMOPIPERAZINES

[75] Inventors: Sohei Tanabe, Higashimurayama; Seiichi Sato, Tokyo; Yoshinori Kyotani, Higashiyamato; Tomio Ohta, Sayama; Yasumi Uchida, Ichikawa, all of Japan

[73] Assignee: Kowa Company, Ltd., Aichi, Japan

[21] Appl. No.: 310,683

[22] Filed: Feb. 15, 1989

[30] Foreign Application Priority Data

Feb. 16, 1988 [JP] Japan ................................. 63-31931

[51] Int. Cl.⁵ .................. C07D 243/08; C07D 241/50; C07D 413/06; C07D 405/08
[52] U.S. Cl. ................................. 540/575; 544/120; 544/360; 544/363; 544/373; 544/374; 544/383
[58] Field of Search ................ 540/575, 386; 544/120, 544/360, 363, 373, 374, 383

[56] References Cited

U.S. PATENT DOCUMENTS 4,051,125 9/1977 Tanaka et al. ....................... 540/575

FOREIGN PATENT DOCUMENTS 0012727 4/1971 Japan .................................. 540/575
3017870 1/1988 Japan .................................. 540/575

Primary Examiner—David B. Springer
Attorney, Agent, or Firm—Wenderoth, Lind & Ponack

[57] ABSTRACT

A propane derivative represented by the following formula

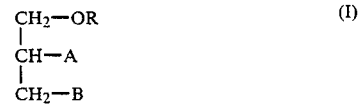

wherein R represents a lower alkyl group; one of A and B represents a group of the formula

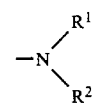

and the other represents a group of the formula

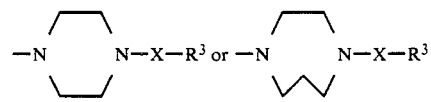

in which $R^1$ and $R^2$ are identical or different and each represents a hydrogen atom, a lower alkyl group, an aryl group or an aralkyl group, $R^3$ represents a substituted or unsubstituted lower alkyl group, a substituted or unsubstituted aryl group or a substituted or unsubstituted heterocyclic group, and X represents a sulfonyl group or a carbonyl group, and an acid addition salt thereof. The compounds provided by this invention have useful biological activities such as the spasmolytic activity on the vascular smooth muscles and anti-platelet aggregatory activity and are useful as drugs for treating cardiovascular diseases such as angina pectoris, cerebral circulation disorder and thrombosis.

6 Claims, No Drawings

PIPERAZINES AND HOMOPIPERAZINES

This invention relates to novel propane derivatives, and more specifically to a propane derivative represented by the following formula $$\begin{array}{c} CH_2-OR \\ | \\ CH-A \\ | \\ CH_2-B \end{array} \quad (I)$$

wherein R represents a lower alkyl group; one of A and B represents a group of the formula

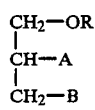

and the other represents a group of the formula

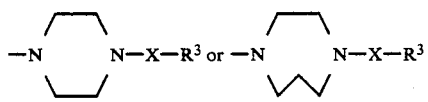

in which $R^1$ and $R^2$ are identical or different and each represents a hydrogen atom, a lower alkyl group, an aryl group or an aralkyl group, $R^3$ represents a substituted or unsubstituted lower alkyl group, a substituted or unsubstituted aryl group or a substituted or unsubstituted heterocyclic group, and X represents a sulfonyl group or a carbonyl group, and an acid addition salt thereof, and to a process for production thereof.

3-iso-Butoxy-2-pyrrolidino-N-phenyl-N-benzyl-proylamine of the following formula

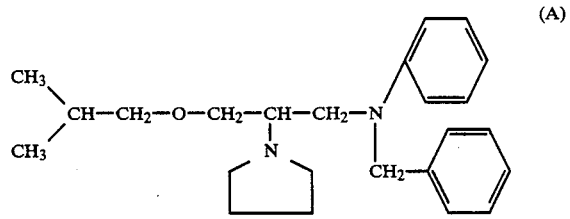

is known as a therapeutic agent for cardiovascular disorders, particularly angina pectoris. (British Patent No. 1,595,031).

The compounds of formula (I) provided by this invention have some useful biological activities such as the spasmolytic activity on the vascular smooth muscles and anti-platelet aggregatory activity and are useful as drugs for treating cardiovascular diseases such as angina pectoris, cerebral circulation disorder and thrombosis.

In the present specification, the term "lower" used to qualify a group or compound, means that the group or compound so qualified has not more than 6, preferably not more than 4, carbon atoms.

The "lower alkyl group" in the present specification may be linear or branched, and includes, for example, methyl, ethyl, propyl, isopropyl, butyl, isobutyl, sec-butyl, tert-butyl, pentyl, isopentyl and hexyl groups.

The "aryl group" may be monocyclic or polycyclic, and have 6 to 20 carbon atoms and includes, for example, phenyl, alpha-naphthyl and beta-naphthyl groups. The "aralkyl group" is an aryl-lower alkyl group in which the lower alkyl and aryl have the above meanings. Examples are benzyl and phenethyl groups, alpha-naphthylmethyl, beta-naphthylmethyl, alpha-naphthylethyl, beta-naphthylethyl.

The "heterocyclic group" includes 4- to 20-membered, preferably 5- to 10-membered heterocyclic groups containing at least 1, preferably 1 to 3, heteroatoms selected from nitrogen, oxygen and sulfur atoms, as the ring members. Specific examples are pyridyl, quinolyl, isoquinolyl, thienyl, furyl, indolyl, piperidino, piperidinyl, morpholino and morpholinyl groups.

Examples of the substituent in the "substituted lower alkyl group" include halogen atoms such as fluorine, chlorine and bromine atoms, lower alkoxy groups such as methoxy, ethoxy, propoxy, isopropoxy, butoxy, isobutoxy and tert-butoxy groups, a nitro group and a nitroxy group. Examples of the substituent in the "substituted aryl group" and the "substituted heterocyclic group" include halogen atoms such as fluorine, chlorine and bromine atoms, lower alkyl groups such as methyl, ethyl, propyl, isopropyl, butyl and tert-butyl groups, lower alkoxy groups such as methoxy, ethoxy, propoxy, isopropoxy, butoxy, isobutoxy and tert-butoxy groups, a nitro group, a cyano group and a hydroxyl group. The aryl group and the heterocyclic group may be substituted by 1 to 3 such substituents.

The substituent A in formula (I) may either be the group

or the group

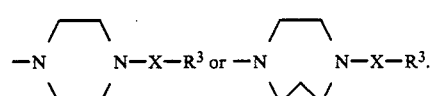

Generally, the substituent A is preferably the substituted amino group. More preferably, in the substituted amino group, $R^1$ is an aralkyl group and $R^2$ is a hydrogen atom or a lower alkyl group. Benzyl amino and N-methylbenzylamino groups are particularly preferred as the substituted amino group.

The latter groups are preferably those in which $R^3$ is a lower alkyl group optionally substituted by a nitroxy group, a phenyl group optionally substituted by a halogen atom or a lower alkoxy group, a naphthyl group optionally substituted by a halogen atom, or an isoquinolyl group.

Specific examples of the compounds of formula (I) are given below in addition to those given in the working examples hereinafter.

1-(6-Nitro-β-naphthylcarbonyl)-4-(3-ethoxy-2-ethylphenylaminopropyl)piperazine, 1-trifluoromethylsulfonyl-4-(3-n-propoxy-2-naphthylaminopropyl)piperazine, 1-thienylsulfonyl-4-[2-(3-isopropoxy-1-naphthylisopropylamino)-propyl]homopiperazine, 1-furylcarbonyl-4-2-(3-n-butoxy-1-diphenylamino)-propyl)piperazine,
1-piperidinocarbonyl-4-[2-(3-sec-butoxy-1-amio)-propyl]-homopiperazine,
1-morfolinosulfonyl-4-[2-(3-tert-butoxy-1-methylamino)-propyl]piperazine,
1-3-(5-chloroindoly)sulfonyl)-4[2-(3-n-pentyloxy-1-diethylamino)-propyl]homopiperazine,
1(5-quinolylcarbonyl)-4-[2-(3-isopentyloxy-1--naphthylmethylamino)-propyl]piperazine,
1-tosyl-4-(3-n-hexyloxy-2-benzylphenylaminopropyl)-homopiperazine, and
1-p-hydroxybenzylsulfonyl-4-(3-isobutoxy-2-benzylmethylaminopropyl)piperazine.

The compounds of formula (I) may exist as acid addition salts. Examples of the acid addition salts are salts with inorganic acids such as sulfuric acid, hydrochloric acid, nitric acid, phosphoric acid and hydrobromic acid and salts with organic acids such as acetic acid, lactic acid, succinic acid, tartaric acid, malic acid, citric acid, methanesulfonic acid, benzenesulfonic acid and toluenesulfonic acid. Pharmaceutically acceptable acid addition salts, are particularly preferred.

The compounds of formula (I) can be produced, for example, by the methods described below.

(1) Production of compounds (I) in which A is the group

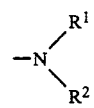

and B is the group

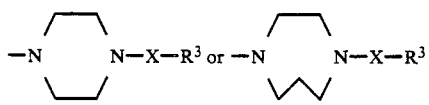

[Compounds of formula (I-1) hereinafer]

In the above formulae, A¹ represents the group

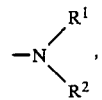

Y represents a halogen atom, a lower alkylsulfonyloxy group or a substituted or unsubstituted arylsulfonyloxy group, n represents a number of 1 or 2, and R, $R^1$, $R^2$, $R^3$ and X are as defined above.

In the method of route (a), the starting compound of formula (II) is first reacted with piperazine or homopiperazine of formula (III). As a result, rearrangement reaction takes place to form the compound of formula (IV). The rearrangement reaction can be advantageously accelerated by converting the secondary hydroxyl group at the 2-position of the starting compound of formula (II) into a group which readily undergoes a nucleophilic reaction, such as a methanesulfonic ester group, a p-toluenesulfonic ester group or a halogen atom before reacting it with the compound (III).

The secondary hydroxyl group at the 2-position may be converted into a methanesulfonate group or a p-toluenesulfonate group in a customary manner. For example, the compound of formula (II) is reacted with a methanesulfonyl halide or a p-touenesulfonyl halide in a solvent in the presence of a base. Examples of the base used in this method include inorganic bases such as sodium hydroxide, potassium hydroxide, sodium carbonate and potassium carbonate, and organic bases such as triethylamine, dimethylaminopyridine, and pyrrolidinopyridine. Examples of the solvent are chloroform, dichloromethane, carbon tetrachloride, benzene, acetone, methyl ethyl ketone, diethyl ether, dioxane, tetrahydrofuran, ethyl acetate, acetonitrile, dimethylformamide and dimethyl sulfoxide. The reaction may be completed in several minutes to several hours at a temperature of about 0° to 100° C.

The reaction of the compound of formula (II) with piperazine or homopiperazine of formula (III) may be conveniently carried out in the aforesaid solvent in the Reaction Scheme 1

Route (a)

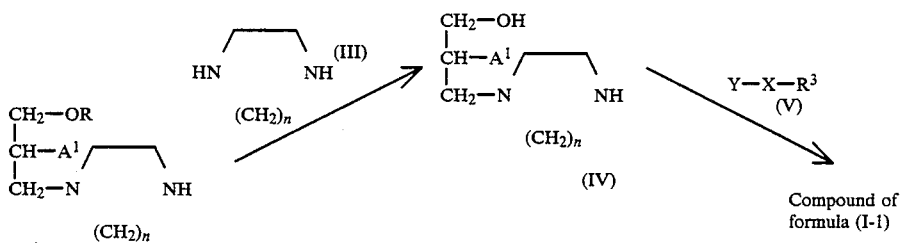

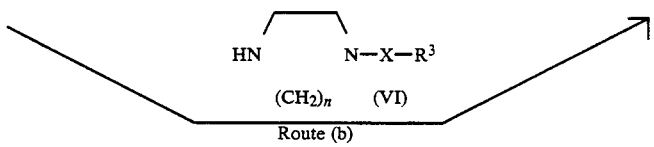

Route (b)

presence of the aforesaid base. The reaction temperature is usually from about 0° C. to the refluxing temperature of the reaction mixture, preferably about 50° to 120° C. The amount of piperazine or homopiperazine used is not critical. Generally, its suitable amount is 1 to 10 moles, preferably 1 to 2 moles, per mole of the compound of formula (II).

The resulting compound of formula (IV) is then reacted with the compound of formula (V). This reaction can be carried out usually at a temperature of about −10 to 100° C., preferably about 0° to 50° C., in the aforesaid solvent in the presence of the aforesaid base. It is convenient to use the compound of formula (V) in an amount of generally 1 to 10 moles, preferably 1 to 2 moles, per mole of the compound of formula (IV). As a result, the desired compound of formula (I-1) can be obtained.

Alternatively, the compound of formula (I-1) may be produced by reacting the starting compound of formula (II) with an N-substituted piperazine or homopiperazine of formula (VI) in accordance with route (b). The reaction of the compound of formula (II) with the compound of formula (VI) may be carried out in the same way as described above with regard to the reaction of the compound of formula (II) with the compound of formula (III) in route (a).

(2) Production of compounds of formula (I) in which A represents the group

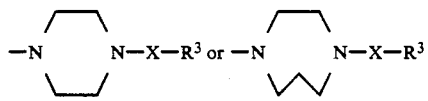

and B represents

[to be referred to as the compound of formula (I-2)]

ment reaction as described with regard to route (a) takes place to form a compound of formula (I-2) in which $R^2$ is a hydrogen atom, i.e. a compound of formula (I-2-a). This reaction can be carried out in the same way as described above with regard to the reaction of the compound (II) with the compound (III) in route (a).

The resulting compound of formula (I-2-a) is then reacted with the compound of formula (IX) to form a compound of formula (I-2) in which $R^2$ represents the above-defined groups other than the hydrogen atom, i.e. a compound of formula (I-2-b). This reaction can be carried out at a temperature of usually about 0° to 150° C., preferably about 50° to 100° C., in the aforesaid solvent and optionally in the presence of the aforesaid base.

Alternatively, the compound of formula (I-2) can be produced by reacting the compound of formula (VII) with a compound of formula (X) in accordance with route (d) in the same way as described above with regard to route (b).

The compounds of formula (I-1) and formula (I-2) can be isolated from the reaction mixture and/or purified by conventional methods such as recrystallization, extraction and chromatography.

As required, the compounds of formula (I) may be converted into acid addition salts by treating them with the aforesaid inorganic acids or organic acids.

The compound of formula (II) or (VII) used as the starting material in the methods described in Reaction Schemes 1 and 2 may easily be produced by, for example, the method shown in Reaction Scheme 3 below.

Reaction Scheme 3

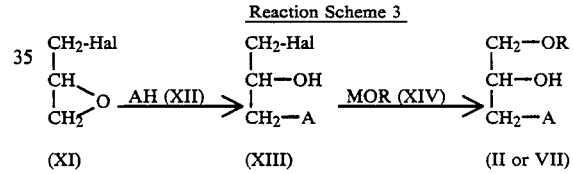

Reaction Scheme 2

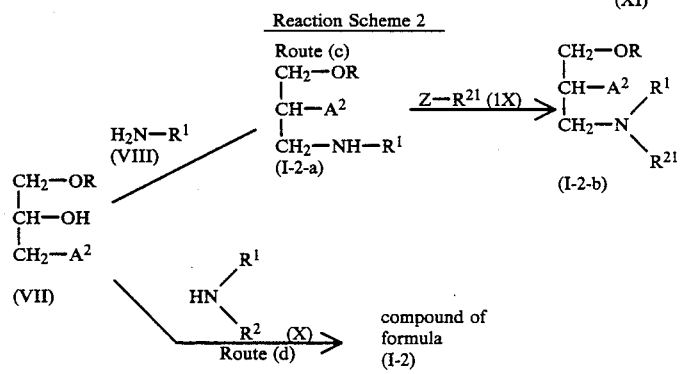

In the formulae, $A^2$ represents the group

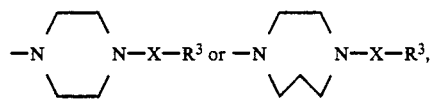

$R^{21}$ represents the groups defined for $R^2$ excepting the hydrogen atom, Z represents a halogen atom, a lower alkylsulfonyloxy group, a substituted or unsubstituted arylsulfonyloxy group or a nitroxy group, and R, $R^1$, $R^2$, $R^3$ and X are as defined hereinabove.

In route (c), the starting compound (VII) is reacted with an amine of formula (VIII). The same rearrange- In the formulae, Hal represents a halogen atom, preferably a chlorine atom, M represents an alkali metal, and A and R are as defined above.

The epihalohydrin of formula (XI) is reacted with the compound of formula (XII) in a customary manner to open the oxirane ring and thus obtain a compound of formula (XIII). This compound is then reacted with an alcoholate of formula (XIV) in a suitable solvent, or treated with a base, for example an alkali metal hydride such as sodium hydride, in an alcohol of the formula ROH. As a result, the compound of formula (II) or (VII) can be obtained.

As stated above, the compounds of formula (I) provided by this invention have excellent biological activities on a cardiovascular system, such as the spasmolytic activity on the vascular smooth muscles and anti-platelet aggregatory activity, and are expected to be useful drugs for preventing and treating diseases such as angina pectoris and cerebral circulation disorder. There is now a tendency that laser angioplasty will be put into practice in the near future for the treatment of arterial thrombosis. The most significant problem is the spasmodic contraction which occurs during the laser angioplasty. Therefore, the compounds (I) of this invention which have spasmolytic activity on blood vessels will effectively support the operation of thrombosis.

The spasmolytic activity on the vascular smooth muscles and anti-platelet aggregatory activity of the compounds of this invention can be demonstrated by the following in vitro and in vivo tests.

(A) Inhibitory activity on spasmodic contraction

Ring segments, 2 mm wide, were prepared from the coronary artery (left circumflex coronary artery or anterior descending artery having a diameter of about 2 to 3 mm isolated from male dogs). The ring segments were each suspended in a Magnus tube filled with 20 ml of the Krebs-Henseleit solution (37° C., 95% $O_2$-5% $CO_2$ were passed) at an initial tension of 2 g. The tension was measured by a U gauge. After standing for more than 30 minutes to stabilize the segments 25 or 50 mM KCl was added 2 to 3 times at intervals of 15 minutes to test the reactivity of the sample segments. 10 mM 3,4-diaminopyridine (a product of Nakarai Chemical Co., Ltd.) was added to those samples which showed a good contracting reaction to induce periodic contraction. When the periodic contraction became nearly constant, test compounds were added cumulatively, and their activity was examined.

(B) Inhibitory effect on ADP-induced platelet aggregation

Rabbit PRP (250 μl) was preincubated with drug samples (10μ) of aqueous solution or 1μl of DMSO solution) at 37° C. for 1 minute, and ADP (2 μm)-induced platelet aggregation was measured by aggregometer (NKK HEMA TRACER1 Model PAT-4M). Inhibitory effects of the drugs were estimated from the standard curve of maximal aggregation.

| Compound No. (Example No.) | Spasmodic contraction inhibitory concentration (mole/liter) | Platelet aggregation inhibitory concentration (mole/liter) Inhibition rate (%) in the parentheses |
|---|---|---|
| 1 | $10^{-6}$ | $10^{-5}$ (12) |
| 2 | $10^{-6}$ | $10^{-4}$ (60) |
| 7 | $10^{-6}$ | $10^{-4}$ (33) |
| 9 | $10^{-5}$ | $10^{-5}$ (8) |
| 10 | $10^{-5}$ | $10^{-4}$ (35) |
| 11 | $10^{-7}$ | $10^{-4}$ (33) |

The following examples illustrate the present invention more specifically.

REFERENTIAL EXAMPLE 1

Production of 3-isobutoxy-2-hydroxy-N-methyl-N-benzylpropylamine (a) Epichlorohydrin (3 g) and 12 g of N-methylbenzylamine were dissolved in 24 ml of methanol. The solution was stirred at room temperature for 30 minutes and then at 50° C. for 30 minutes. The reaction mixture was concentrated to dryness under reduced pressure. The residue was purified by silica gel column chromatography [solvent: chloroform/ammonia-saturated methanol (50:1)] to give 7 g of 3-chloro-2-hydroxy-N-methyl-N-benzylpropylamine as a colorless oil.

$^1$H-NMR: δ $CDCl_3$
2.25 (3H, s, $NCH_3$)

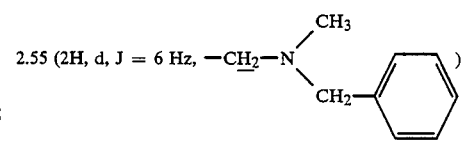
2.55 (2H, d, J = 6 Hz, $-C\underline{H}_2-N$...)

3.70–3.50 (4H, m, $-C\underline{H}_2-Cl$,

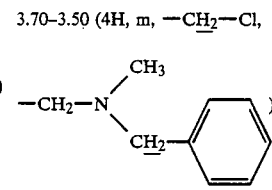

4.10–3.70 (1H, m, > $C\underline{H}-OH$)
7.33 (5H, br.s, aromatic H)

(b) 50% sodium hydride (742 g) was dissolved in 18 ml of isobutanol, and 1.1 g of the chloro-substituted product obtained in (a) above was aided to the solution. The mixture was stirred at room temperature for 30 minutes and then at 90° C. for 1 hour. The reaction mixture was concentrated to dryness under reduced pressure. The residue was dissolved in ethyl acetate, washed with water and dried, followed by evaporation of the solvent. The residue was purified by silica gel column chromatography (solvent: chloroform) to give 864 mg of the captioned compound as a colorless oil.

$^1$H-NMR: δ $CDCl_3$

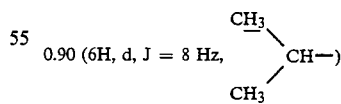
0.90 (6H, d, J = 8 Hz, $CH-$)

2.25 (3H, s, $NCH_3$)

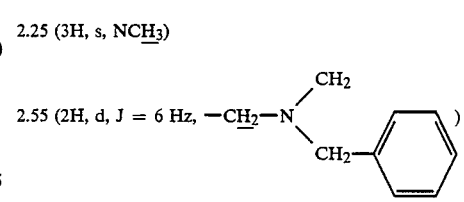
2.55 (2H, d, J = 6 Hz, $-C\underline{H}_2-N$...)

3.70–3.50 (4H, m, $-C\underline{H}_2-Cl$,

-continued

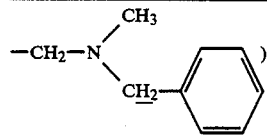
)

4.10–3.70 (1H, m, \CH—OH)
           /

7.33 (5H, br.s, aromatic)

REFERENTIAL EXAMPLE 2
Production of 1-benzenesulfonyl-4-(3-isobutoxy-2-hydroxypropyl)-piperazine (a) Epichlorohydrin (0.5 g) and 3.7 g of 1-benzenesulfonylpiperazine were reacted and worked up in the same way as in Referential Example 1 to give 1.7 g of 1-benzenesulfonyl-4-(3-chloro-2-hydroxypropyl)piperazine as a colorless powdery crystal having a melting point of 136 to 137° C.

IR: $\nu_{max}^{KBr}$, cm$^{-1}$
3368, 3238, 1345, 1169, 754
$^1$H-NMR: δ CDCl$_3$

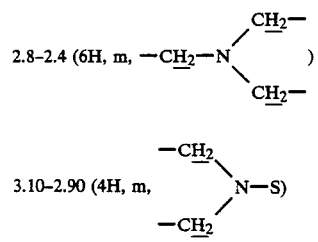

3.6–3.5 (2H, m, —CH$_2$Cl)
3.9–3.8 (1H, m, —CH$_2$OH)
7.8–7.5 (5H, m, aromatic H)

Elemental analysis for C$_{13}$H$_{19}$ClN$_2$O$_3$S:

|  | C | H | N |
|---|---|---|---|
| Calculated (%) | 48.98 | 6.01 | 8.79 |
| Found (%) | 48.96 | 5.89 | 8.75 |

(b) The chloro-substituted product obtained in (a) above (1.3 g) and sodium isobutoxide (obtained by dissolving 0.59 g of 50% sodium hydride in 15 ml of isobutanol) were reacted and worked up in the same way as in Referential Example 1, (b) to give 1.3 g of the captioned compound as a colorless powdery crystal having a melting point of 79° to 80° C.

IR: $\nu_{max}^{KBr}$, cm$^{-1}$
3493, 3296, 1361, 1171
$^1$H-NMR: δ CDCl$_3$

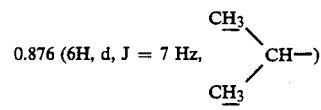

-continued 3.10–2.90 (4H, m, 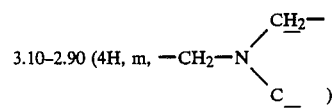 )

3.90–3.70 (1H, m, \CH—OH)
           /

7.80–7.50 (5H, m, aromatic H)

EXAMPLE 1
Production of 1-(3,4-dimethoxybenzenesulfonyl)-4-(3-isobutoxy-2-methylbenzylaminopropyl)-piperazine (a) The alcohol compound used in Referential Example 1 (48 mg) and 29 mg of triethylamine were dissolved in 0.5 ml of tetrahydrofuran. With ice cooling and stirring, 33 mg of methanesulfonyl chloride was added, and the mixture was stirred at room temperature for 30 minutes. After the reaction, the insoluble matter was removed by filtration, and the mother liquor was concentrated to dryness under reduced pressure. The residue was dissolved in 0.5 ml of dimethylformamide. Piperazine (69 mg) and 111 mg of potassium carbonate were added, and the mixture was stirred at 60° C. for 1.5 hours. The reaction mixture was poured into water, and extracted with ethyl acetate. The extract was washed with an aqueous solution of sodium chloride, and dried. Then, the solvent was evaporated. The residue was purified by preparative thin-layer chromatography [carrier: silica gel; developing solvent: chloroform/ammonia-saturated methanol (10:1) to give 37 mg of 1-(3-isobutoxy-2-methylbenzylaminopropyl)piperazine as a colorless oil.

$^1$H-NMR: δ CDCl$_3$

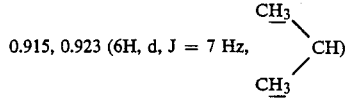

0.229 (3H, s, NCH$_3$)

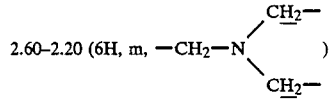

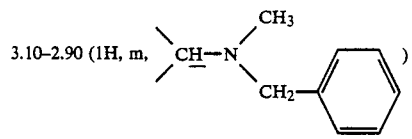

7.40–7.20 (5H, m, aromatic H)

(b) The compound obtained in (a) above (129 mg) was dissolved in 2 ml of tetrahydrofuran, and 45 mg of triethylamine was added. With ice cooling and stirring, 90 mg of 3,4-dimethoxybenzenesulfonyl chloride was added, and the mixture was stirred at room temperature for 5 minutes. The reaction mixture was concentrated to dryness under reduced pressure. The residue was dissolved in ethyl acetate, washed with an aqueous solution of sodium chloride, and dried, followed by evaporation of the solvent. The residue was purified by silica gel column chromatography [solvent: chloroform/methanol (100:1)] to give 147 mg of the captioned compound as a pale yellow oil.

IR: $\nu_{max}^{CHCl_3}$, cm$^{-1}$
1587, 1504, 1484, 1272, 1158, 1136

$^1$H-NMR: δ CDCl$_3$

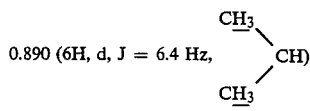
0.890 (6H, d, J = 6.4 Hz,

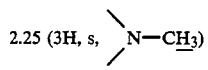
2.25 (3H, s,

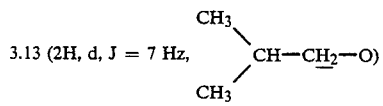
3.13 (2H, d, J = 7 Hz,

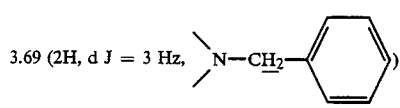
3.69 (2H, d J = 3 Hz, 3.94, 3.96 (6H, s, OCH$_3$)
7.40–6.99 (8H, m, aromatic H)

EXAMPLE 2

Production of 1-benzenesulfonyl-4-(3-isobutoxy-2-methylbenzylaminopropyl)homopiperazine The alcohol compound obtained in Referential Example 1 (510 mg) and 591 mg of 4-benzenesulfonyl-1-homopiperazine were reacted and worked up in the same way as in Example 1, (a) to give 577 mg of the captioned compound as an oil.

IR: $\nu_{max}^{film}$, cm$^{-1}$
1445, 1331, 1157, 726

$^1$H-NMR: δ CDCl$_3$

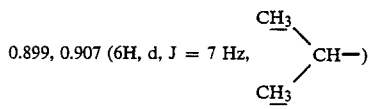
0.899, 0.907 (6H, d, J = 7 Hz,

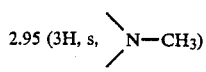
2.95 (3H, s,

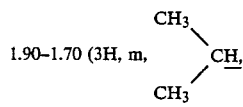
1.90–1.70 (3H, m,

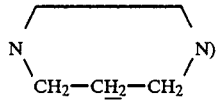
3.70 (2H, s, 7.80–7.20 (10H, m, aromatic H)

EXAMPLE 3

Production of 1-benzenesulfonyl-4-[2-(3-isobutoxy-1-benzylamino)-propyl]piperazine The 1-benzenesulfonyl-4-(3-isobutoxy-2-hydroxypropyl)piperazine (1.8 g), obtained in Referential Example 2 and 1.2 g of benzylamine were reacted and worked up in the same way as in Example 1, (a) to give 0.7 g of the desired free base. Dihydrochloride of this compound was a slightly yellow powder having a melting point of 60° to 90° C. (decomp.).

IR: $\nu_{max}^{KBr}$, cm$^{-1}$
3400, 1455, 1168, 737

$^1$H-NMR: δ CDCl$_3$

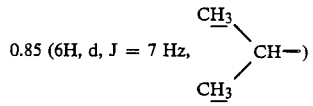
0.85 (6H, d, J = 7 Hz,

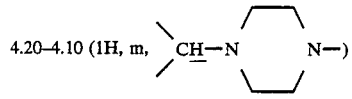
4.20–4.10 (1H, m, 7.90–7.40 (10H, m, aromatic H)

Elemental analysis for C$_{24}$H$_{35}$N$_3$O$_3$S·2HCl·1/2H$_2$O:

|  | C | H | N |
|---|---|---|---|
| Calculated (%) | 54.65 | 7.26 | 7.97 |
| Found (%) | 54.46 | 7.13 | 8.27 |

EXAMPLE 4

Production of 1-benzenesulfonyl-4-[2-(3-isobutoxy-1-methylbenzylamino)propyl]-piperazine (I)

The compound obtained in Example 3 (480 mg), 55 mg of methyl iodide and 149 mg of potassium carbonate were added to 11 ml of acetone, and the mixture was stirred at room temperature for 1 hour. The insoluble matter was removed from the reaction mixture by filtration, and the solvent was evaporated. The residue was purified by silica gel column chromatography [solvent: chloroform/methanol (100:1)] to give 300 mg of the captioned compound as a colorless oil.

IR: $\nu_{max}^{film}$, cm$^{-1}$

-continued
1446, 1350, 1168, 740, 577
¹H-NMR: δ CDCl₃
0.856 (6H, d, J = 7 Hz, 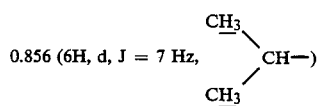)
2.17 (3H, s, NCH₃)
-continued
3.10–3.00 (1H, m, 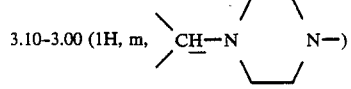)
3.40–3.30 (2H, m, 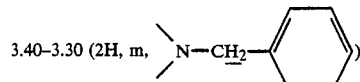)
7.80–7.20 (10H, m, aromatic H)
EXAMPLES 5–15
The compounds of formula (I) tabulated below were produced in the same way as in Examples 1 to 4.

| Example | R | A | B | Property | IR $\nu_{max}$ | $^1$H-NMR $\delta$ |
|---|---|---|---|---|---|---|
| 5 | -CH$_2$-CH(CH$_3$)$_2$ | -N(CH$_3$)-CH$_2$-C$_6$H$_5$ | piperidine-N-SO$_2$-C$_6$H$_4$-Cl (4-Cl) | white powder (dihydrochloride) | KBr 1455, 1354, 1165, 760 | CDCl$_3$<br>0.962, 0.965 (6H, d, J = 7 Hz, CH(CH$_3$)$_2$)<br>2.84 (3H, s, NCH$_3$)<br>4.41 (2H, br.s, N-CH$_2$-C$_6$H$_5$) |
| 6 | " | " | piperidine-N-SO$_2$-CH$_2$-C$_6$H$_5$ | white powder (dihydrochloride) | 1454, 1331, 1155, 942, 699 | 0.959 (6H, d, J = 7 Hz, CH(CH$_3$)$_2$)<br>2.84 (3H, s, N-CH$_3$)<br>4.24 (2H, s, SO$_2$-CH$_2$-C$_6$H$_5$)<br>4.42 (2H, s, N-CH$_2$-C$_6$H$_5$)<br>7.75-7.30 (10H, m, aromatic H) |
| 7 | " | " | piperidine-N-COCH$_2$CH$_2$ONO$_2$ | oil | Film 1635, 1418, 1279, 856 | CDCl$_3$<br>0.916, 0.923 (6H, d, J = 7 Hz, CH(CH$_3$)$_2$)<br>2.30 (3H, s, NCH$_3$)<br>2.74 (2H, t, J = 7 Hz, N-CO-CH$_2$-CH$_2$-)<br>4.81 (2H, t, J = 7 Hz, -CH$_2$-CH$_2$-ONO$_2$)<br>4.75-4.70 (2H, m, N-CH$_2$-C$_6$H$_5$)<br>7.40-7.20 (5H, m, aromatic H) |

-continued

| Example | R | A | B | Property | IR $\nu_{max}$ | $^1$H-NMR δ |
|---|---|---|---|---|---|---|
| 8 | -CH$_2$-CH(CH$_3$)(CH$_3$) | -N(CH$_3$)-CH$_2$-Ph | piperidine-N-CO-Ph (N-phenoxycarbonyl piperazine) | oil | 1638, 1445, 1113, 1000 | 0.912, 0.918 (6H, d, J = 7 Hz, CH$_3$/CH$_3$/CH); 2.30 (3H, s, NCH$_3$); 3.10-2.95 (1H, m, CH$_2$-N(CH$_3$)-CH$_2$-Ph); 3.17 (2H, d, J = 7 Hz, CH$_3$/CH-CH$_2$-O/CH$_3$); 3.85-3.70 (2H, m, N-CH$_2$-Ph); 7.40 (5H s, aromatic H); 7.35-7.25 (5H, m, aromatic H) |
| 9 | " | " | 5-chloro-naphthalene-1-SO$_2$-N-piperazine | white powder (dihydrochloride) | KBr 1456, 1275, 1146, 942 | DMSO-d$_6$ 0.88 (6H, d, J = 7 Hz, CH$_3$/CH/CH$_3$); 2.65 (3H, s, NCH$_3$); 3.10-2.90 (1H, m, CH-N); 4.40-4.10 (2H, m, N-CH$_2$-Ph); 8.55-7.10 (11H, m, aromatic H); Film CDCl$_3$ |

-continued

| Example | R | A | B | Property $\nu^{IR}_{max}$ | $^1$H-NMR δ |
|---|---|---|---|---|---|
| 10 | -CH$_2$-CH(CH$_3$)CH$_3$ | -N(CH$_3$)-CH$_2$-C$_6$H$_5$ | piperazine-N-SO$_2$CH$_3$ | oil; 1450, 1342, 1158, 958 | 0.917, 0.923 (6H, d, J = 7 Hz, CH$_3$-CH-CH$_3$); 2.31 (3H, s, N-CH$_3$); 2.78 (3H, s, -SO$_2$-CH$_3$); 3.74 (2H, br.s, N-CH$_2$-); 7.40–7.20 (5H, m, aromatic) |
| 11 | " | " | piperazine-N-SO$_2$-C$_6$H$_5$ | white powder (dihydrochloride); KBr 1455, 1354, 1165, 760 | CDCl$_3$; 0.962 (6H, d, J = 7 Hz, CH$_3$-CH-CH$_3$); 2.84 (3H, s, N-CH$_3$); 4.41 (2H, br.s, N-CH$_2$-) |
| 12 | " | " | piperazine-N-SO$_2$-(4-F-C$_6$H$_4$) | oil; Film 2940, 2840, 1594, 1494, 1352 | CDCl$_3$; 0.91 (6H, d, J=7 Hz, CH$_3$-CH-CH$_3$); 2.28 (3H, s, N-CH$_3$); 2.3–2.8 (6H, m, CH$_2$-N(CH$_2$)-CH$_2$); 2.8–3.3 (7H, m, CH$_2$-N-S, CH-CH$_2$-O, CH$_2$-CH-N) |

-continued

| Example | R | A | B | Property $\nu^{IR}_{max}$ | $^1$H-NMR δ |
|---------|---|---|---|--------------------------|--------------|
| 12 | —CH$_2$—CH(CH$_3$)CH$_3$ | —N(CH$_3$)—CH$_2$—Ph | 4-F-C$_6$H$_4$—SO$_2$—N(piperazine) | oil / 1169, 733, 546 | 3.72 (2H, s, —N—CH$_2$—Ph); 7.2–7.48 (7H, m, aromatic H); 7.72–7.98 (2H, m, aromatic H) |
| 13 | " | " | isoquinoline-5-SO$_2$—N(piperazine) | / 3913, 3850, 1450, 1362, 1327, 1320, 1211, 1160, 1131, 946 | 0.90 (6H, d, J = 8 Hz, CH(CH$_3$)$_2$); 2.23 (3H, s, N—CH$_3$); 2.24–2.68 (6H, m, —CH$_2$— and N(CH$_2$)$_2$); 3.02–3.30 (6H, m, N—S, N(CH$_2$—CH$_2$—O)); 3.38, 3.50 (2H, dd, J = 10 Hz, —CH$_2$—CH—N); 3.66, 3.70 (2H, d, J = 15 Hz, N—CH$_2$—Ph); 7.74 (1H, t, J = 8 Hz, aromatic H); 8.24 (1H, d, J = 8 Hz, aromatic H); 8.38 (1H, d, J = 8 Hz, aromatic H); 8.57 (1H, d, J = 7 Hz, aromatic H); 8.70 (1H, d, J = 7 Hz, aromatic H); CDCl$_3$ |

-continued

| Example | R | A | B | Property $\nu_{max}^{IR}$ | 1H-NMR δ |
|---------|---|---|---|---|---|
| 14 | —CH$_2$—CH(CH$_3$)(CH$_3$) | isoquinoline-5-sulfonyl-piperazinyl | —N(CH$_3$)—CH$_2$—C$_6$H$_5$ | oil | 0.83 (6H, d, J = 7 Hz, CH(CH$_3$)CH$_3$)<br>2.17 (3H, s, N—CH$_3$)<br>2.40-2.84 (5H, m, CH—CH$_2$—N—CH$_2$, CH$_2$)<br>2.90-3.20 (6H, m, CH—CH$_2$—O, CH$_2$—N—S, CH$_2$)<br>3.46 (2H, s, N—CH$_2$—C$_6$H$_5$)<br>7.23 (5H, s, aromatic H)<br>7.72 (1H, t, J = 8 Hz, aromatic H)<br>8.22 (1H, d, J = 8 Hz, aromatic H)<br>8.37 (1H, d, J = 8 Hz, aromatic H)<br>8.56 (1H, d, J = 7 Hz, aromatic H)<br>8.68 (1H, d, J = 7 Hz, aromatic H)<br>9.35 (1H, s, aromatic) |
| 15 | —CH$_3$ | —N(CH$_3$)—CH$_2$—C$_6$H$_5$ | phenylsulfonyl-piperazinyl | oil<br>Film<br>1445<br>1349<br>1167<br>947<br>740 | CDCl$_3$<br>2.25 (3H, s, N—CH$_3$)<br>2.60-2.20 (6H, m, CH$_2$ × 3)<br>3.20 (4H, J = 4 Hz, CH$_2$—N—S, CH$_2$)<br>3.30 (3H, s, OCH$_3$)<br>3.66 (2H, s, N—CH$_2$—C$_6$H$_5$)<br>7.80-7.20 (10H, m, aromatic H) |

We claim:
1. A compound represented by the following formula

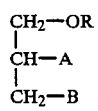 (I)

wherein R represents a $C_1$-$C_6$ alkyl group; one of A and B represents a group of the formula

and the other represents a group of the formula

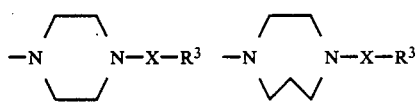

in which $R^1$ and $R^2$ are identical or different and each represents a hydrogen, a lower alkyl, a phenyl or napthyl which is optionally substituted by 1 to 3 substituents selected from the group consisting of halogen, $C_1$-$C_6$ alkyl, $C_1$-$C_6$ alkoxy, nitro, cyano and hydroxy or $C_1$-$C_6$ alkyl substituted by a phenyl or naphthyl which is optionally substituted by 1 to 3 substituents selected from the group consisting of halogen, $C_1$-$C_6$ alkyl, $C_1$-$C_6$ alkoxy, nitro, cyano and hydroxy, $R^3$ represents a $C_1$-$C_6$ alkyl group unsubstituted or substituted by a member selected from the group consisting of halogen, $C_1$-$C_6$ alkoxy, nitro and nitroxy, a phenyl or naphthyl unsubstituted or substituted by 1 to 3 substituents selected from the group consisting of halogen, $C_1$-$C_6$ alkoxy, nitro, cyano and hydroxy or a heterocyclic group which is selected from the group consisting of pyridyl, quinolyl, isoquinolyl, thienyl, furyl, indolyl, piperidino, piperidinyl, morpholino and morpholinyl groups and which is optionally substituted by 1 to 3 substituents selected from the group consisting of halogen, $C_1$-$C_6$ alkyl, $C_1$-$C_6$ alkoxy, nitro, cyano and hydroxy, and X represents a sulfonyl or a carbonyl, and a pharmaceutically acceptable acid addition salt thereof.

2. The compound of claim 1 in which A represents the group

and B represents the group

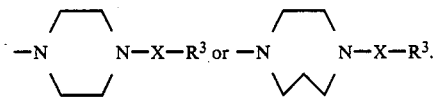

3. The compound of claim 1 in which A represents the group

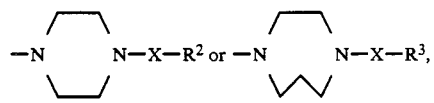

and B represents the group x

4. The compound of claim 1 in which A represents a benzylamino or N-methylbenzylamino group.

5. The compound of claim 1 in which $R^3$ represents a lower alkyl group which may be substituted by a nitroxy group; a phenyl group which may be substituted by a halogen atom or a lower alkoxy group; a naphthyl group which may be substituted by a halogen atom; or an isoquinolyl group.

6. The compound according to claim 1 which is: 1-(3,4-dimethoxybenzenesulfonyl)-4-(3-isobutoxy-2-methylbenzylaminopropyl)piperazine, 1-benzenesulfonyl-4-(3-isobutoxy-2-methylbenzylaminopropyl)-homopiperazine, 1-(2-nitroxyethylcarbonyl)-4-(3-isobutoxy-2-methyl benzylaminopropyl)-piperazine, 1-[α-(5-chloronaphthyl)sulfonyl]-4-(3-isobutoxy-2-methylbenzylamino propyl)piperazine, 1-methylsulfonly-4-(3-isobutoxy-2-methylbenzylaminopropyl)piperazine, and 1-benzenesulfonyl-4-(3-isobutoxy-2-methylbenzylaminopropyl)piperazine.

* * * * *